United States Patent [19]

Sarrine

[11] Patent Number: 5,179,960
[45] Date of Patent: Jan. 19, 1993

[54] BIOLOGICAL FLUID COLLECTION AND DELIVERY APPARATUS AND METHOD

[75] Inventor: Robert J. Sarrine, Beaumont, Tex.

[73] Assignee: Helena Laboratories Corporation, Beaumont, Tex.

[21] Appl. No.: 746,412

[22] Filed: Aug. 16, 1991

[51] Int. Cl.⁵ ................................................ A61B 5/00
[52] U.S. Cl. ..................................... 128/764; 128/765
[58] Field of Search ........................ 128/760, 763–765, 128/770; 604/317, 403, 411, 415

[56] References Cited

U.S. PATENT DOCUMENTS

| | | | |
|---|---|---|---|
| 2,594,621 | 4/1952 | Derrick | 128/765 |
| 3,604,410 | 9/1971 | Whitacre | 128/764 |

FOREIGN PATENT DOCUMENTS

| | | | |
|---|---|---|---|
| 0045863 | 2/1982 | European Pat. Off. | 128/764 |
| 2409040 | 7/1979 | France | 128/765 |

Primary Examiner—Max Hindenberg
Attorney, Agent, or Firm—Spencer, Frank & Schneider

[57] ABSTRACT

A biological fluid collection and dispensing apparatus for attachment to a test tube includes a pump and a cannula assembly housed partially within the pump including a fluid transfer cannula and a vent cannula. Biological fluid or other fluid can be both collected and delivered with the apparatus, which apparatus may remain attached to the test tube during any processing of the collected biological fluid sample.

10 Claims, 4 Drawing Sheets

FIG. 3
FIG. 4
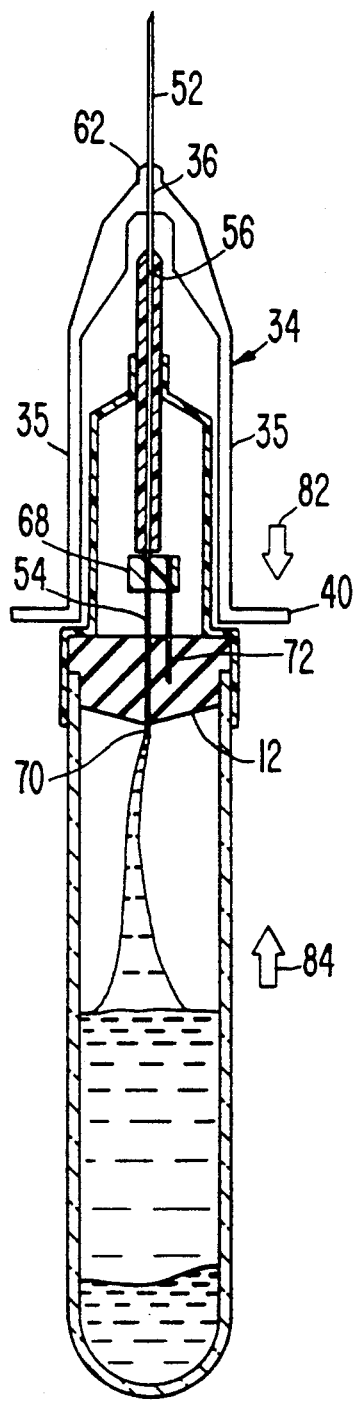
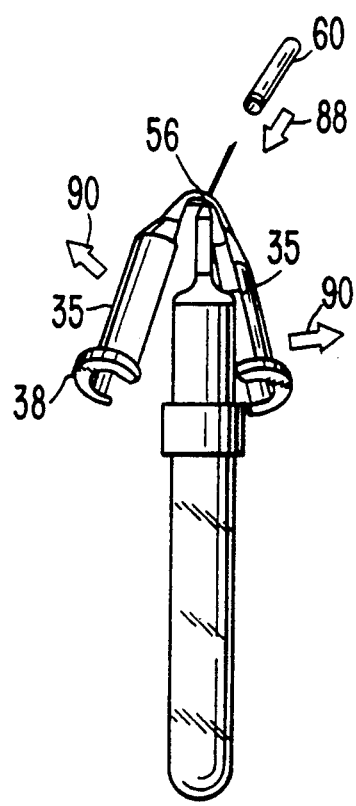

FIG. 5
FIG. 6
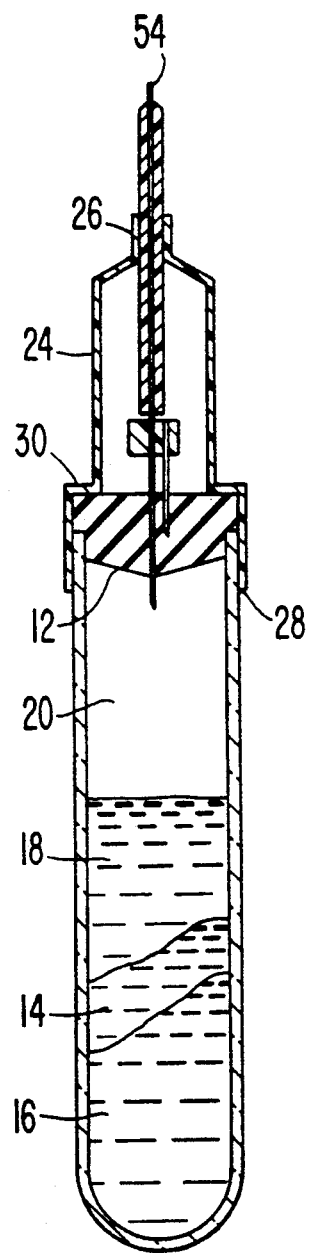
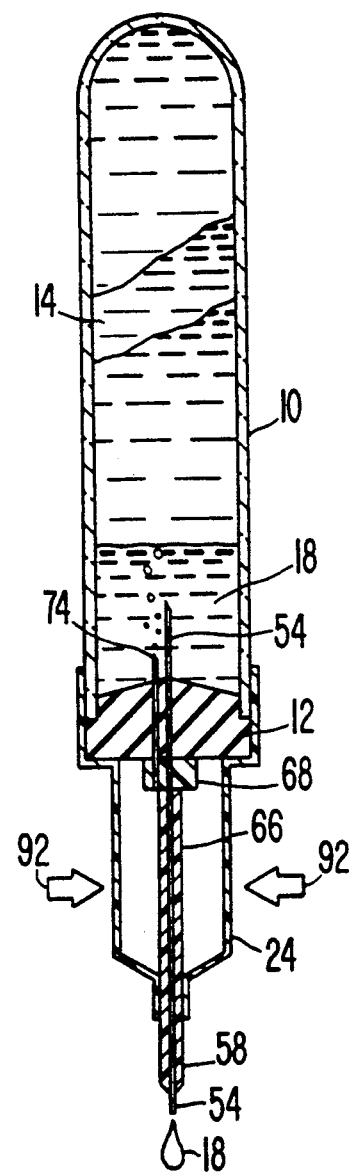

BIOLOGICAL FLUID COLLECTION AND DELIVERY APPARATUS AND METHOD

CROSS-REFERENCE TO RELATED APPLICATIONS

The present application includes subject matter in common with prior applications Ser. Nos. 07/504,597, filed Apr. 4, 1990, which is a continuation-in-part of application Ser. No. 07/382,760, filed Jul. 21, 1989, which is a continuation-in-part of application Ser. No. 07/208,447 filed Jun. 20, 1988, and prior applications Ser. Nos. 07/256,243 filed Sep. 30, 1988 and 07/089,275 filed Aug. 25, 1987, now U.S. Pat. No. 4,925,065, which were continuations of application Ser. No. 07/000,266 filed Jan. 2, 1987, now U.S. Pat. No. 4,811,866, all of which are hereby incorporated by reference.

BACKGROUND OF THE INVENTION

The invention relates generally to methods and apparatus for drawing or collecting blood or other biological fluid from a patient and thereafter dispensing the biological fluid in aliquots for analytical testing. More specifically, the present invention relates to a one-piece disposable apparatus including all of the features needed to draw such fluid and thereafter dispense the fluid.

The separation and analysis of chemical substances provides valuable quantitative and qualitative data for use by researchers and health care providers. Many assaying techniques have been developed which utilize sensitive chemical tests and sensitive instruments to detect both normal and abnormal components of biological fluids such as blood, urine and spinal fluid. In particular, the analysis of samples of these fluids reveals information which is critical to the proper diagnosis and treatment of many disorders. To perform such an analysis, a biological sample is typically withdrawn from the patient into a test tube or vacuum draw collection tube. The biological sample may be subjected to centrifugation. Then the biological sample is dispensed, in suitable aliquots, for testing. In the example of withdrawing blood from a patient, centrifugation separates the serum from the red blood cells and, thereafter, the amount of serum protein, protein-bound iodine, sodium, triglycerides, salicylate, uric acid and the like may all be determined through the analysis of the blood components.

After a biological sample is withdrawn from a patient into a test tube or collection tube, a technician must dispense aliquots or small quantity samples from the test tube. The test tube, of course, is initially sealed to prevent (a) contamination of the sample by ambient constituents and (b) to prevent substances in the sample from entering the atmosphere and/or adversely affecting the technician. Upon removing the conventional stopper from a test tube, the sample is again subject to possible contamination and a phenomenon known as aerosoling occurs. Aerosoling is the expulsion into the air, in the vicinity of the test tube, of minute quantities of the contents of the test tube and is caused by the force of removal of the stopper from the test tube. The removal of the stopper subjects the technician to the risk of exposure to whatever virus, bacteria or the like is carried in the biological sample.

The concern about exposure to the HIV virus has resulted in the adoption of numerous safety precautions in connection with the handling of biological fluids including products for dispensing biological fluids from a test tube without the need for removal of the stopper.

SUMMARY OF THE INVENTION

The present invention utilizes a new and different approach to the problems described above by eliminating the need for separate fluid withdrawal and fluid dispensing apparatus thus further minimizing the risk of contamination of the sample and further minimizing the risk of exposing the technician to the sample.

The present invention relates to a new and improved apparatus which provides for both biological fluid withdrawal into a sealed container and biological fluid dispensing from the sealed container.

It is therefore an object of the invention to provide an efficient and inexpensive apparatus for biological fluid collection and dispensing.

It is a further object of the invention to provide a single assembly that performs both biological fluid collection and dispensing functions.

It is yet another object of the invention to provide a single apparatus for withdrawal of biological fluids such as blood, spinal fluids or the like into a sealed container, retaining such fluids for processing in the sealed container, and thereafter for dispensing the biological fluids in aliquots through the seal of the container.

The above and other objects are accomplished according to an embodiment of the invention by the provision of a biological fluid collection apparatus for attachment to a test tube including a flexible member such as a bulb pump, a cover on said flexible member, and a cannula including first and second portions, the first portion extending through the cover and the second portion extending along the flexible member, biological fluid being drawn through the first and second portions of the cannula into a sealed test tube, the cover and the first portion of the cannula being removed, and the biological fluid thereafter being dispensed through the second portion of the cannula.

BRIEF DESCRIPTION OF THE DRAWINGS

The foregoing objects and advantages of the invention, together with other objects and advantages which may be attained by its use, will become more apparent upon reading the following detailed description of the invention taken in conjunction with the drawings. In the drawings, wherein like reference numerals identify corresponding components:

FIG. 3 is a cross-sectional partly diagrammatic view of the invention for the withdrawal of a biological fluid from a patient;

FIG. 4 is a diagrammatic illustration of the removal of further portions of the invention after biological fluid has been withdrawn from a patient such that the biological fluids may be subjected to processing;

FIG. 5 is a cross-sectional illustration of the invention after the biological fluid has been centrifuged;

FIG. 6 is a cross-sectional illustration of the dispensing of the biological fluid according to the present invention.

DETAILED DESCRIPTION OF THE INVENTION

Figure 1:
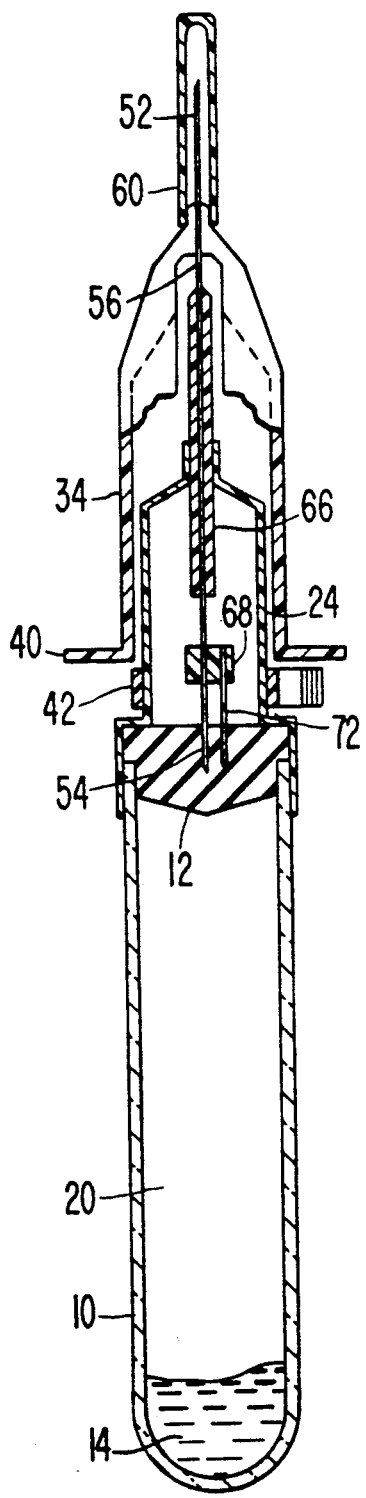
FIG. 1 is a cross-sectional view of an embodiment of the invention.

Referring first to FIG. 1 the present invention is illustrated attached to a test tube or collection tube 10 of the type which is sealed by a puncturable, reusable, resilient stopper or closure 12 as is conventional. The sealed test tube may be under vacuum, such as a Vacutainer test tube marketed by Becton-Dickinson, and if the test tube is to be used for blood serum separation, then, in addition to an anticoagulant in the test tube as is conventional, a conventional gel-like separator plug 14 is included in the test tube. Referring briefly to FIG. 5, if blood has been introduced into the test tube and thereafter centrifuged, red blood cells 16 will be positioned in the bottom of the test tube, on one side of the separator plug 14, and serum 18 will be on the opposite side of the plug 14. An unfilled space 20 may exist between the serum and the underside of the stopper 12.

A pump means 24 is mounted to the test tube 10. Specifically, with reference again to FIG. 1, a pump means is illustrated in the form of a flexible, elongated, resilient bulb having a first, preferably constricted end 26 and a second open end 28. A shoulder 30 is formed in the bulb intermediate the two ends, the shoulder being adjacent the second end 28, and the shoulder and second end are configured to frictionally receive and retain the closed top of the test tube 10.

A cover 34 is positioned on the flexible member or pump 24. The cover 34 is formed as a hollow member having two elongated, hollow semi-hemispherical legs 35 and a first end 36 where the two legs are joined. The two legs 35 of the cover terminate in a second open end 38 and an outwardly extending flange 40 is provided at the second end of the cover. A collar 42 is provided on the outside of the pump 24 intermediate the flange 40 of the cover and the shoulder 30 of the pump means. The collar 42, which maintains the cover and pump means longitudinally spaced apart, terminates in an outwardly extending tab 44 to facilitate removal of the collar.

The apparatus of the present invention includes a cannula 50, which may also be considered a fluid flow path or fluid transfer path, the cannula having a first portion 52 and a second portion 54, the first and second portions being longitudinally aligned to provide a continuous flow path. The first and second cannula portions are preferably formed as a single, continuous cannula including a score line or area of reduced thickness 56 therebetween. The first cannula portion 52 terminates in a sharpened tip 58 which extends through the first end 36 of the cover 34. An elongated protective cap 60 is provided to protect against damage to the sharpened tip 58 and to protect against injury therefrom, such caps being conventional in connection with syringes and the like, the cap being frictionally retained on an axial proterberance 62 which is formed on the first end 36 of the cover 34 and extends in a direction away from the second end 38 of the cover.

The second portion 54 of the cannula 50 extends through an elongated hollow cannula housing 66, the cannula housing with the cannula therein extending through the constricted open first end 26 of the pump means. A fluid-tight seal is formed between the open first end 26 of the pump means and the exterior of the cannula housing 66. The cannula housing extends longitudinally into the pump means 24 and the second portion 54 of the cannula extends completely through the hollow cannula housing, and through a hollow cannula support member 68, and terminates in a sharpened point 70. The cannula support member 68 has two spaced apart apertures therethrough, the cannula second portion 54 being force fit through one of said apertures, as previously mentioned, and a vent cannula 72, having a sharpened tip or end 74, is force fit through the second aperture in the cannula support member. Collectively cannula 50 and vent cannula may be considered as cannula means. Housing 66 and cannula support member 68 may be considered as housing means.

Figure 2:
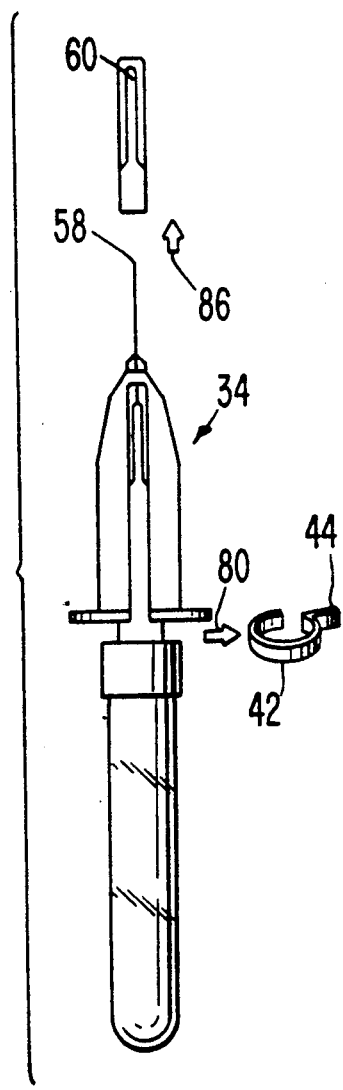
FIG. 2 is a diagrammatic illustration of the removal of portions of the invention such that blood or other biological fluids may be withdrawn from a patient.

The operation of the apparatus will now be explained. With the collar 42 in position intermediate the shoulder 30 of the pump means and the flange 40 of the cover (see FIG. 1), the sharpened tip 58 of the second cannula portion 54 and the sharpened tip 74 of the vent cannula are both positioned within the rubber stopper of the test tube 10. The first use of the apparatus of the present invention is to withdraw biological fluid such as blood from a patient. Collar 42 is removed by grasping the tab 44, as diagrammatically illustrated by arrow 80, (see FIG. 2) and collar 42 may be discarded, and the cap 60 is removed as illustrated diagrammatically by the arrow 86 in FIG. 2 thus exposing the sharpened tip 58 of the cannula such that biological fluid may be withdrawn from a patient, and the tip is inserted into the patient. There, cover 34 is moved axially of the test tube toward the stopper 12 such as by applying force on the flange 40, in the direction of arrow 82 in FIG. 3, until the underside of the flange 40 abuts the top of the shoulder 30. This may be accomplished easily by grasping the apparatus and applying a force with the first and second fingers of the hand against the flange 40 and pushing against the bottom of the test tube, toward the stopper 12, in the direction of arrow 84 illustrated in FIG. 3. Thus relative axial force in two directions has been described but it must be realized that one of the parts may be maintained stationary and the other part moved in relation to the stationary part. The movement of the cover as described moves the cannula means and housing means axially toward the test tube, and the extent of movement is such that the sharpened tip 70 of cannula 50 will pierce through the stopper 12 but the tip 74 of the vent cannula 72 will not extend through the stopper 12. The cap 60 is removed as illustrated diagrammatically by the arrow 86 in FIG. 2 thus exposing the sharpened tip 58 of the cannula such that biological fluid may be withdrawn from a patient.

After the completion of withdrawal of biological fluid from the patient (and the sharpened cannula tip withdrawn from the patient) cap 60 may be positioned over the cannula tip, as illustrated diagrammatically by the arrow 88 in FIG. 4. Then the bifurcated cover 34 is removed, as illustrated diagrammatically by the arrows 90 in FIG. 4, by applying laterally outward force on each of the legs of the cover at a distance remote from the first end 36 of the cover. The cover removing force additionally functions to sever the cannula at the score line 56 such that the cover and first cannula portion are disengaged from the apparatus and may be discarded. The test tube, with the pump means 24 and second cannula portion attached, may be subjected to centrifuging operations.

When it is desired to remove aliquots of the biological fluid from the test tube, the cannula housing 66 must be moved axially inwardly until one end (the end closer to the stopper 12) of the cannula housing 66 contacts the cannula support member 68. Continued movement of the cannula housing 66 axially inwardly, in contact with the cannula support member 68, causes the cannula support member 68 to move axially toward the test tube stopper 12 until bottom of the cannula support member 68 contacts the top of the stopper 12. The degree or extent of movement of the cannula support member 68 is such that the tip 74 of the vent cannula 72 will extend completely through the stopper 12. Then the test tube, with pump means attached, is inverted and the pump means actuated. In the illustrated embodiment the flexible bulb would be compressed by a laterally inward force in the direction illustrated by arrows 92 in FIG. 6. Compression of the bulb causes air within the pump means 24 to flow through the vent cannula into the interior of the test tube 10. This pressurizes the fluid within the test tube such that biological fluid is pumped outwardly through the cannula second portion 54 to be dispensed in a drop-by-drop manner. After the fluid has been dispensed, the apparatus is again "inverted", thus restoring the apparatus to its original, upright position, and the pump means 24 released. Ambient air is drawn through the cannula 50 into the air space 20 interiorly of the test tube 10 and flows upwardly through vent cannula 72 to again fill the pump means 24 with air. Thereafter, by again inverting the apparatus and actuating the pump means 24, fluid may be dispensed through cannula 50.

Figure 7:
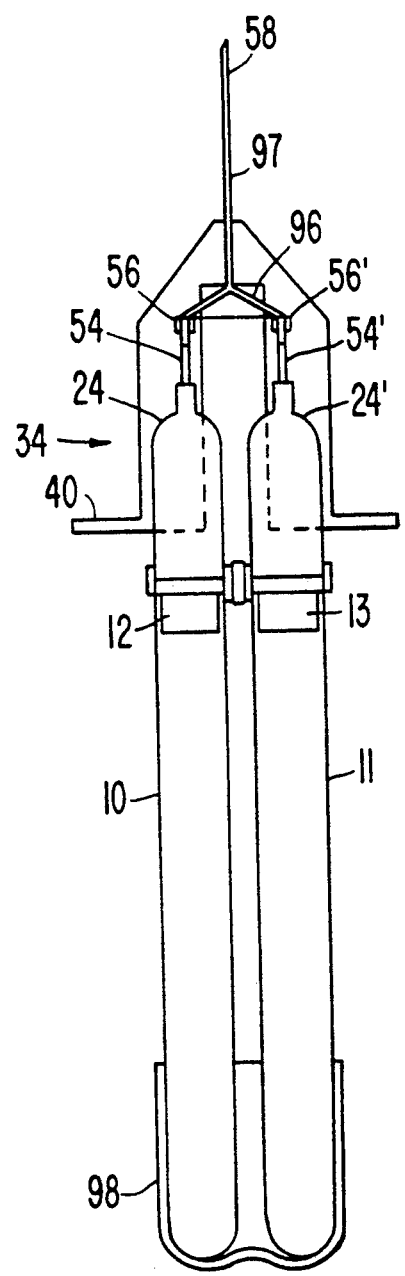
FIG. 7 is an illustration of a second embodiment of the present invention, partially broken away, wherein multiple samples are withdrawn from a patient according to the principles of the present invention.

In numerous situations more than a single test tube of biological fluid is to be withdrawn from a patient. The present invention contemplates such use and reference should now be had to FIG. 7. In the embodiment of FIG. 7, two test tubes 10, 11 are illustrated, each closed by a stopper 12, 13 respectively. The first portion of the cannula, i.e., the portion of the cannula between the score line 56 and the tip 58 in the embodiment of FIGS. 1-6 is now formed as a Y-shaped conduit 96 formed, for example, of metal or plastic, where the single leg of the Y-shaped conduit is connected to a cannula portion 97 including a sharpened tip 58, and the two legs of the Y-shaped conduit each include score lines 56, 56' which are connected, respectively, to the second portion 54, 54' of cannulas extending through respective pump means 24, 24' attached to each test tube. The cover 34 is, of course, of larger configuration to receive two test tubes and a holder 98 is provided to receive and retain the bottoms of two test tubes. Each of the test tubes includes its own pump means, cannula housing, cannula support member and vent cannula.

The operation of the apparatus of FIG. 7 will now be explained. During the withdrawal of fluid from the patient, fluid will flow through the sharpened tip 58, through cannula portion 97, through the Y-shaped conduit 96, through the second portions 54, 54' of the cannulas, and into the test tubes. When the cover is removed, thus breaking the cannulas at the score line 56, 56', the Y-shaped conduit 96 is removed with the cover and sharpened tip portion of the cannula. The holder 98 is removed and, thereafter, each test tube, with its respective pump means, may be separately processed and used to dispense fluid.

In a preferred embodiment, the cannulas are formed of stainless steel and the remaining components (other than the glass test tube and rubber stopper) will be formed of plastic. More specifically, the pump means may be formed of a resilient, flexible plastic such as polyethylene, cap 60 may be formed of a material such as polypropylene or styrene, and the remaining members such as cover 34, cannula housing 66, cannula support member 68, collar 42, and conduit 96 will preferably be formed of styrene. The foregoing materials are exemplary for the purpose of illustrating the principles of the present invention and thus the foregoing should not be construed as limitations on the present invention.

It should be further understood that the apparatus of the present invention is adapted to be attached to a conventional test tube by the technician. Alternatively, the apparatus of the present invention may be attached to a test tube at the time the test tube is initially placed under partial vacuum.

It will be understood that the above description of the present invention is susceptible to various modifications, changes, and adaptations, and the same are intended to be comprehended within the meaning and range of equivalents of the appended claims.

What is claimed is:

1. Apparatus for drawing biological fluid from a patient into a test tube, the test tube being sealed with a puncturable closure, and for thereafter dispensing the biological fluid through the closure and from the test tube comprising:
   a flexible member adapted to be attached to said test tube;
   a removable cover on said flexible member;
   a cannula having a first portion extending through said cover and a second portion extending along said flexible member;
   said cannula second portion having a tip insertable through said closure;
   said cannula first portion having a tip extending through said cover for withdrawal of biological fluid from a patient, such that said biological fluid flows through said cannula into said sealed test tube; and
   said cover being removable from said flexible member such that upon flexing said flexible member, biological fluid flows from said sealed test tube through said cannula.

2. The apparatus of claim 1 wherein said flexible member is a pump means.

3. The apparatus of claim 1 further including a test tube having a closure and wherein said cannula second portion tip is inserted into said test tube closure.

4. A biological fluid collection and dispensing apparatus for attachment to a test tube comprising:
   a flexible bulb pump; and
   cannula means disposed partially within the bulb pump, the cannula means including a fluid transfer cannula extending axially relative to the bulb pump and a vent cannula disposed adjacent to the fluid transfer cannula, and housing means within the bulb pump for supporting the cannula means.

5. The apparatus of claim 4, further comprising:
   a removable cover, the flexible bulb pump disposed within the cover; and
   the fluid transfer cannula being scored at a point external to the bulb pump;
   whereby, when the cover is removed, a portion of the fluid transfer cannula is removed at said score point.

6. The apparatus of claim 4 further including a test tube having a closure and wherein said cannula second portion tip is inserted into said test tube closure.

7. The apparatus of claim 4 for attachment to two test tubes further comprising;

a second flexible bulb pump; and second cannula means disposed partially within the second bulb pump, the second cannula means including a second fluid transfer cannula extending axially relative to the second bulb pump and a second vent cannula disposed adjacent to the second fluid transfer cannula, and second cannula supporting means within the second bulb pump for supporting the second cannula means.

8. The apparatus of claim 7 further including conduit means interconnecting the first and second fluid transfer cannulas.

9. A method of using the apparatus of claim 4, comprising:

attaching a test tube having a rubber stopper to the apparatus opposite the first end of the fluid transfer cannula so that a second end of the fluid transfer cannula pierces and extends through the rubber stopper completely;

inserting a first end of the fluid transfer cannula into a patient;

collecting a quantity of biological fluid into the test tube through the fluid transfer cannula;

removing the first end of the fluid transfer cannula from the patient;

removing the cover and removing the first end of the fluid transfer cannula at the score point;

moving the cannula support means towards the test tube so that the vent cannula pierces completely through the rubber stopper;

inverting the apparatus; and flexing the bulb pump to deliver a portion of the biological fluid in the test tube through the fluid transfer cannula.

10. A biological fluid collection and dispensing apparatus comprising:

a partially evacuated glass test tube sealed with a rubber stopper;

a cannula assembly attached to the test tube and rubber stopper, said cannula assembly including a flexible plastic bulb designed to removably mate with the test tube and stopper, a fluid transfer cannula and a vent cannula, the fluid transfer cannula extending axially through the flexible plastic bulb, the vent cannula disposed within the plastic bulb adjacent to the fluid transfer cannula, first adjacent ends of both cannulas partially piercing the rubber stopper when attached to the test tube, a second opposite end of the fluid transfer cannula having a score point disposed thereon external to the plastic bulb;

cannula support means for movably supporting said cannulas with respect to the plastic bulb;

a concentric cover partially and removably covering the plastic bulb and having finger stops for facilitating manually activated piercing of the rubber stopper by the fluid transfer cannula during use of the apparatus in fluid collection, the removal of said concentric cover causing the fluid transfer cannula to break at the score point thereon; and a collar positioned exteriorly of the plastic bulb axially intermediate the test tube and the cover, for preventing the cannulas from prematurely piercing through the rubber stopper of the test tube.

* * * * *